(12) United States Patent
van Zelm et al.

(10) Patent No.: US 9,823,248 B2
(45) Date of Patent: Nov. 21, 2017

(54) METHODS AND KITS FOR DETECTING IGE-EXPRESSING B CELLS

(75) Inventors: Menno Cornelis van Zelm, Rotterdam (NL); Jacobus Johannes Maria van Dongen, Rotterdam (NL); José Alberto Orfao de Matos Correia e Vale, Salamanca (ES)

(73) Assignees: ERASMUS UNIVERSITY MEDICAL CENTER ROTTERDAM, Rotterdam (NL); UNIERSIDAD DE SALAMANCA, Salamanca (ES)

( * ) Notice: Subject to any disclaimer, the term of this patent is extended or adjusted under 35 U.S.C. 154(b) by 0 days.

(21) Appl. No.: 14/358,287

(22) PCT Filed: Nov. 15, 2011

(86) PCT No.: PCT/NL2011/050781
§ 371 (c)(1),
(2), (4) Date: Jun. 9, 2014

(87) PCT Pub. No.: WO2013/073932
PCT Pub. Date: May 23, 2013

(65) Prior Publication Data
US 2014/0315749 A1 Oct. 23, 2014

(51) Int. Cl.
*G01N 33/564* (2006.01)
*G01N 33/569* (2006.01)
*G01N 33/68* (2006.01)
*G01N 33/58* (2006.01)

(52) U.S. Cl.
CPC ..... *G01N 33/56972* (2013.01); *G01N 33/564* (2013.01); *G01N 33/582* (2013.01); *G01N 33/6854* (2013.01); *G01N 2800/24* (2013.01)

(58) Field of Classification Search
CPC ........... G01N 33/56972; G01N 33/564; G01N 33/582; G01N 33/6854; G01N 2800/24
See application file for complete search history.

(56) References Cited

U.S. PATENT DOCUMENTS

| 5,786,161 A * | 7/1998 | Irsch ............... G01N 33/54326 435/7.24 |
| 2006/0073611 A1* | 4/2006 | Grainger ............... C07K 1/047 436/518 |

OTHER PUBLICATIONS

Perez-Andres et al. Human Peripheral Blood B-Cell Compartments: A Crossroad in B-Cell Traffic. Cytometry Part B: Clinical Cytometry 78B (Suppl. 1): S47-S60 (published online Aug. 26, 2010).*

(Continued)

*Primary Examiner* — Gail R Gabel
(74) *Attorney, Agent, or Firm* — Hoffmann & Baron, LLP

(57) ABSTRACT

The invention relates to the field of medical diagnostics. In particular, it relates method and kits for identification and classification of IgE-related diseases, e.g. Type I hypersensitivity, as well as for monitoring of treatment efficacy, for instance anti-IgE therapy. Provided is a multi-color flow cytometric method for analyzing memory B cell and plasma cell subsets in a biological sample, comprising staining the sample with a panel of fluorochrome-conjugated antibodies comprising antibodies against IgM, IgA, IgG, IgD and IgE; an antibody against a B cell marker and an antibody against the CD38 antigen; subjecting the sample to flow cytometry and gating for lymphocytes based on forward scatter and side scatter pattern; gating the lymphocytes for expression of the B cell specific marker and CD38 to discriminate between $CD38^{dim}$ memory B cells and $CD38^{hi}$ plasma cells; and quantitating the IgE+ cells within the memory B cell population and/or the plasma cell population by the negative selection of cells expressing IgM, IgA, IgG and/or IgD and the positive selection of IgE expressing cells.

17 Claims, 9 Drawing Sheets

(56) References Cited

OTHER PUBLICATIONS

Takahama et al, "Murine IgG1 and IgE Memory B Cells", Cellular Immunology, vol. 157, pp. 369-380; 1994.
van Dongen et al, "Design and standardization of PCR primers and protocols for detection of clonal immunoglobulin and T-cell receptor gene recombinations in suspect lymphoproliferations: Report of the BIOMED-2 Concerted Action BMH4-CT98-3936", Leukemia vol. 17, pp. 2257-2317; 2003.
Andersen et al, "Deficiency of somatic hypermutation of the antibody light chain is associated with increased frequency of severe respiratory tract infection in common variable immunodeficiency", Blood vol. 105, No. 2; Jan. 2005.
van Zelm et al, "Replication history of B lymphocytes reveals homeostatic proliferation and extensive antigen-induced B cell expansion", The Journal of Experimental Medicine, vol. 204, No. 3; Mar. 2007.
Lefranc et al, "IMGT, the international ImMunoGeneTics information system", Nucleic Acids Research, vol. 37; 2009.
Mohapatra et al, "Immunotheraphy for allergies and asthma: present and future", Science Direct, vol. 10, pp. 276-288; 2010.
Brightbill et al, "Antibodies specific for a segment of human membrane IgE deplete IgE-producing B cells in humanized mice", The Journal of Clinical Investigation, vol. 120, No. 6; Jun. 2010.
Perez-Andres et al, "Human Peripheral Blood B-Cell Compartments: A Crossroad in B-Cell Traffic", Clinical Cytometry Part B, pp. S47-S60; 2010.
Berkowska et al, "Human Memory B Cells Originate From Three Distinct Germinal Center-Dependent and -Independent Maturation Pathways", Blood, vol. 118:8, pp. 2150-2157; 2011.
Lowe et al, "Omalizumab decreases IgE production in patients with allergic (IgE-mediated) asthma; PKPD analysis of a biomarker, total IgE", British Journal of Clinical Pharmacology, vol. 72.2, pp. 306-320; 2011.

\* cited by examiner

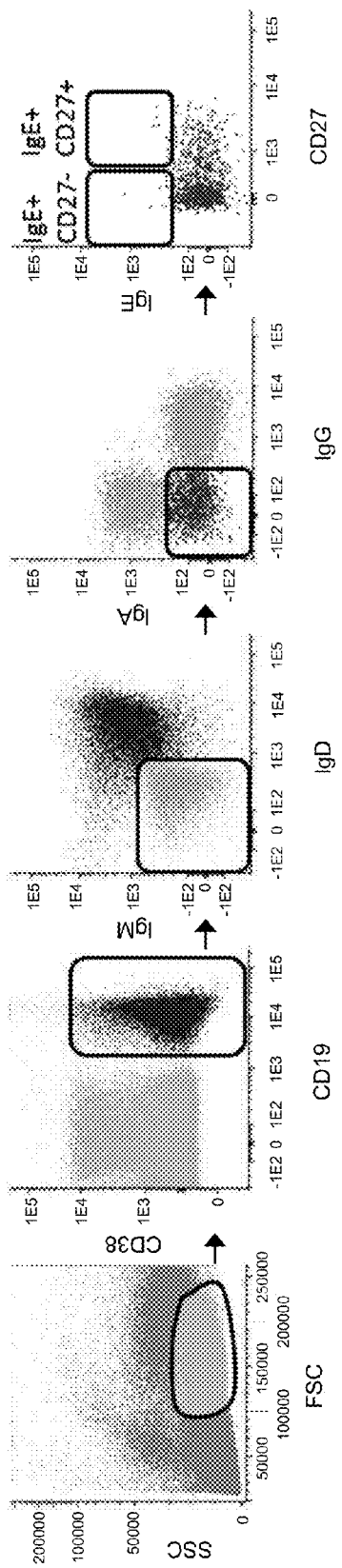
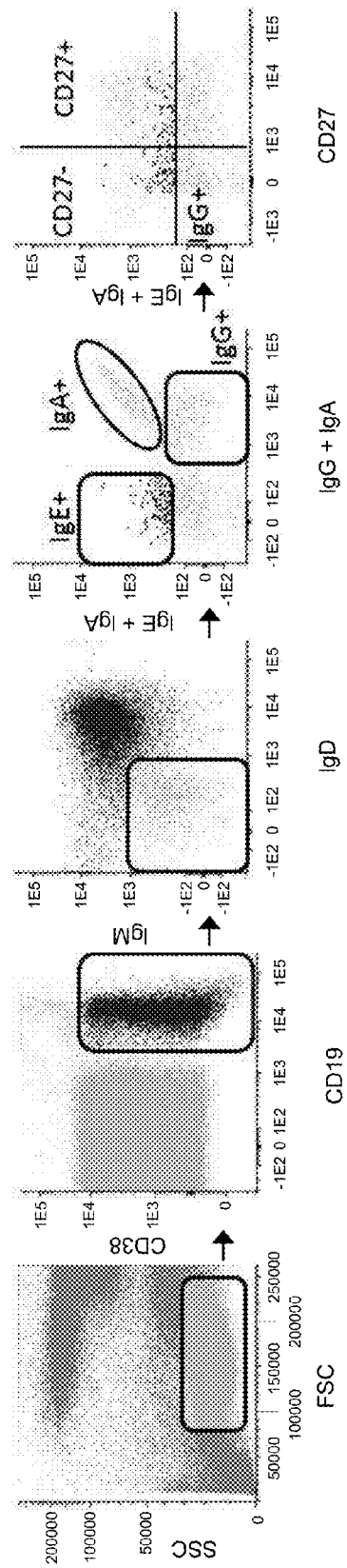
Fig. 1A
Fig. 1B

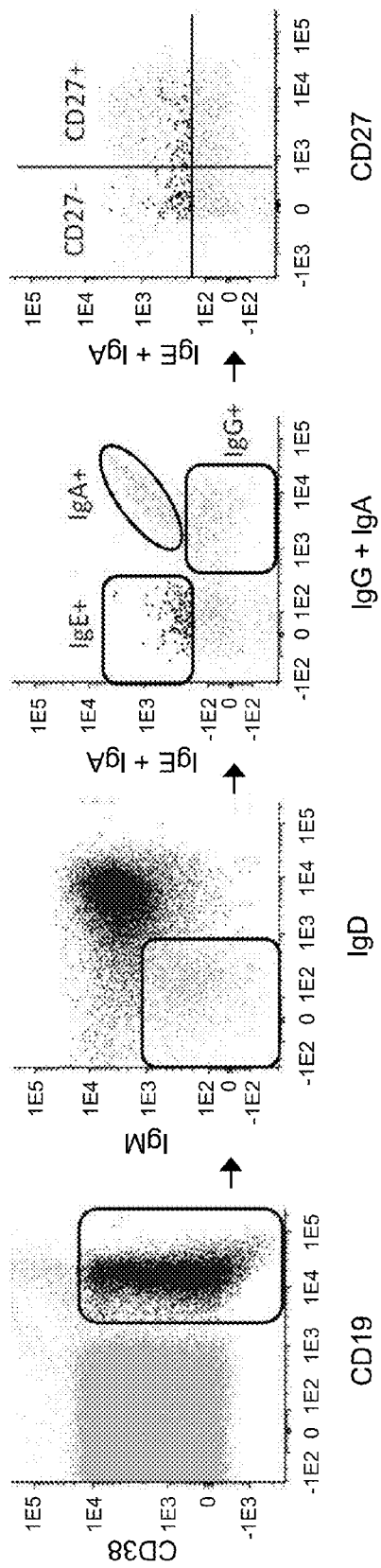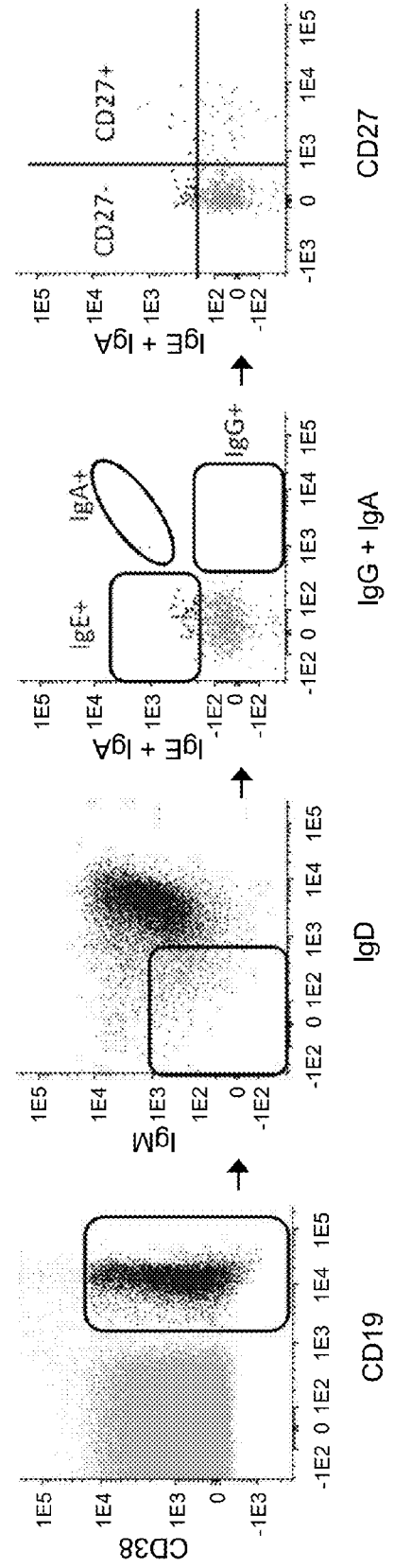

METHODS AND KITS FOR DETECTING IGE-EXPRESSING B CELLS

This application is the U.S. National Phase of, and Applicants claim priority from, International Patent Application Number PCT/NL2011/050781 filed 15 Nov. 2011, the contents of which is incorporated herein by reference.

The invention relates to the field of medical diagnostics. In particular, it relates to methods and kits for identification and classification of IgE-related diseases, e.g. Type I hypersensitivity, as well as for monitoring treatment efficacy, such as anti-IgE therapy.

Immunoglobulin E (IgE) is one of the antibody classes (known as "isotypes") found only in mammals. IgE is capable of triggering the most powerful immune reactions. Most of our knowledge of IgE has come from research into the mechanism of a form of allergy known as type I hypersensitivity. IgE production by B cells requires a physical interaction with T cells, involving a number of surface adhesion molecules, as well as the soluble factors IL-4 and IL-13 produced by T cells, basophils and mast cells.

Type I hypersensitivity disorders (such as allergic rhinitis, asthma, systemic anaphylaxis, and atopic dermatitis) are associated with antibody production (IgE and IgG) and are distinguished by the different types of antigens recognized at the different classes of antibody involved. Type I hypersensitivity reactions underlie all atopic and many allergic disorders. The terms atopy and allergy are often used interchangeably but are different. Atopy is an exaggerated IgE-mediated immune response; all atopic disorders are type I hypersensitivity disorders. Allergy is any exaggerated immune response to a foreign antigen regardless of the mechanism. Thus, all atopic disorders are considered allergic, but many allergic disorders (e.g., hypersensitivity pneumonitis) are not atopic.

The main mediator of type I hypersensitivity responses is IgE, which has a physiological role in immune responses to parasitic worms. Healthy individuals have very low IgE concentrations in serum, because most IgE is bound to the IgE high affinity receptor FcεRI on mast cells and basophils. Antigen recognition and consequently cross-linking of IgE bound to mast cells and basophils leads to the local release of molecules—inflammatory mediators (e.g. histamine and leukotrienes)—, enzymes and cytokines, which together result in the induction of an inflammatory response and the recruitment of cells important in the clearance of a parasitic infection.

When such a response is directed against harmless environmental particles, which are abundantly present in human surroundings, this results in the induction of a type I hypersensitivity response. Diagnosis of patients with immediate IgE-mediated hypersensitivity is currently based on serum IgE levels, local allergic responses in the skin (skin prick test) and/or the presence of reactive IgE-loaded basophils in peripheral blood—basophil activation test (BAT). Treatment of allergic diseases (reviewed in Mohapatra et al. Curr Opin Pharmacol 10:276-288) is mainly focused on reducing serum IgE levels or downstream IgE-mediated responses. Additionally, therapeutic approaches have been developed to reduce the initial IgE synthesis by directing the immune system from TH2-mediated IgE-inducing responses to TH1-mediated responses, or by depleting IgE-producing cells by anti-IgE antibodies such as Omalizumab, Xolair). These therapies aim at reducing the concentrations of free serum IgE. However, recent evidence indicates that the beneficial effect might actually be the result of reduced IgE production (Low P J and Renard. Br J Clin Pharmacol 72:306-320).

Interestingly, the mechanisms by which allergic IgE responses are generated and their specific relevance in allergic diseases currently remain largely unknown. All antibodies, including IgE, are produced by terminally differentiated B cells, called plasma cells. B cells are generated in bone marrow from hematopoietic stem cells. Precursor B cells undergo stepwise rearrangements of their Ig loci. Since every B cell generates a unique Ig molecule, the combined repertoire of all B cells to recognize antigens is enormous (estimated to be $>10^{12}$). Only precursor B cells that have generated a functional Ig molecule will mature and migrate to peripheral lymphoid organs. Subsequently, only those B cells that recognize antigen with their Ig molecule and that get sufficient help from other immune cells (such as T cells) or their secreted products (such as cytokines) will proliferate, and optimize antigen affinity by the introduction of mutations in their Ig genes (somatic hypermutation; SHM). Additionally, these activated B cells will be able to modify the isotype of their Ig molecule from IgM and IgD, to IgG, IgA or IgE (class switch recombination; CSR). The isotype decision is influenced by the local environment in which the B cell is activated: specifically IL-4 and IL-13 can induce switching to IgE. Finally, these B cells will differentiate into Ig producing plasma cells or long-lived memory B cells that will respond to a secondary encounter with the same antigen.

IgM, IgG and IgA expressing B cells can be readily detected in tissue or blood of healthy children and adults. These consist of both plasma cells and memory B cells. In contrast, IgE-expressing B cells are very scarce. Still, IgE transcripts have been detected in various tissues and in blood of healthy controls and allergic subjects. This indicates that IgE can be produced both systemically from plasma cells in bone marrow and locally from plasma cells in mucosal tissue. Furthermore, several studies have shown signs of active Ig-class switch recombination to IgE in bronchial and nasal mucosa. Whether these responses generate IgE memory B cells remains unclear. The kinetics of IgE responses upon secondary encounter suggest a role for IgE memory, but the cells responsible for it have never been detected.

It is therefore the aim of the present invention to detect and characterize IgE-expressing memory B cells and plasma cells in tissues such as tonsil, lymph node, bronchial, nasal and gut biopsies and in neonatal cord blood, bone marrow and peripheral blood samples. In particular, the inventors sought for an approach that can be used not only for (early) identification and classification of patients with atopy, but also to monitor treatment of atopy patients with anti-IgE therapy.

These goals were met by the provision of a new flow cytometry-based procedure to reliably detect and quantify IgE+ memory B cells and IgE+ plasma cells. Using the proposed approach IgE memory B cells can be quantified and their tissue origin and maturation pathway can be determined in patients with type I hypersensitivity responses. Furthermore, the success of anti-IgE treatment (e.g. with Omalizumab/Xolair, or with 47H4 targeting the M1' domain of human membrane IgE) can be readily determined by quantification of the decrease in circulating IgE+ memory B cells and plasma cells.

Accordingly, the invention relates to a multi-color flow cytometric method for analyzing memory B cell and plasma cell subsets in a biological sample, comprising the steps of:

(i) staining the sample with a panel of fluorochrome-conjugated antibodies comprising antibodies against IgM, IgA, IgG, IgD and IgE; an antibody against a B cell marker; and an antibody against the CD38 antigen;

(ii) subjecting the sample to flow cytometry and gating for lymphocytes based on forward scatter and side scatter pattern;

(iii) gating the lymphocytes for expression of the B cell specific marker and CD38 to discriminate between $CD38^{dim}$ memory B cells and $CD38^{hi}$ plasma cells; and (iv) quantitating the IgE+ cells within the memory B cell population and/or the plasma cell population by the negative selection of cells expressing IgM, IgA, IgG and/or IgD and the positive selection of IgE expressing cells.

A method of the invention can be used for a wide variety of (human) biological samples known or suspected to contain IgE+ B cells. The biological sample is for example blood, bone marrow, lymphoid tissue, tears, cerebrospinal fluid, saliva or fluid from skin vesicles. The tissue may be selected from tonsil, lymph node, bronchial, nasal or gut biopsy. The sample may be pretreated, purified and/or processed otherwise by any conventional procedure known in the art to be of benefit for detecting B cells.

The biological sample is contacted with a panel of fluorochrome-conjugated antibodies under conditions suitable for antibody binding to the respective antigens. Any pan-B-cell marker may be used. Typically, the B cell marker is the CD19, CD20, CD79a or CD22 antigen. Preferably, it is the CD19 antigen. Fluorochrome-labeled antibodies for use in a method or kit of the invention can be prepared according to routine techniques or they can be commercially obtained from various sources.

For practical reasons it is preferred to contact the sample simultaneously with all antibodies i.e. with an antibody cocktail. However, it is also envisaged to add the antibodies in two or more consecutive steps. For example, a two-step incubation may be performed when both surface membrane and intracellular stainings are involved. In such cases, first the surface membrane staining and subsequently (after fixation and permeabilization) the cytoplasmic staining can be performed. In case unlabeled antibodies are being used, even multiple incubation steps are needed: 1, unlabeled antibody/ies; 2, second step reagents; 3, blocking step; 4, directly conjugated antibodies. However, such complex staining is generally not preferred in routine diagnostics.

The antibodies are provided with a detectable label that allows for their separate detection and quantitation by flow cytometry. Detectable (e.g., fluorochrome) labels are known in the art. For example, the panel of differentially-labeled antibody reagents comprises a combination of compatible fluorochromes selected from fluorescein isothiocyanate (FITC), phycoerythrin (PE), peridin chlorophyll protein (PerCP), allophycocyanin (APC), alexa fluor 488, alexa 647, alexa 710, alexa fluor 405, cyanin 5 (Cy5), Cyanin 5.5 (Cy5.5), pacific blue (PacB), horizon violet 450 (HV450), pacific orange (PacO), horizon-V500 (HV500), Krome Orange, Brilliant Violet (BV) 412, Orange Cytognos (OC) 515, quantum dots and conjugates thereof coupled with PE, to APC or to PerCP (e.g. PE/Cy5, PE/Cy5.5, PE/Cy7, PerCP/Cy5.5, APC/Cy7, PE-Texas Red) or any additional compatible fluorochrome or fluorochrome tandem.

In a specific aspect, two antibodies selected from the group consisting of anti-IgA, anti-IgE and anti-IgG are conjugated to the same fluorochrome, preferably to FITC or PE. This allows for the inclusion of a further fluorochrome-conjugated reagent (e.g. antibody or antigen) in an 8-color flow cytometric procedure. Because each B cell can only express a receptor of the IgA, IgE or IgG isotype, we combined these three antibodies in two channels. In one embodiment, the antibodies against IgA and IgE are both conjugated to the same first fluorochrome, and the IgA and IgG antibodies are both conjugated to the same second fluorochrome (Table 1). In another embodiment, the antibodies against IgG and IgE are both conjugated to the same first fluorochrome, and the IgG and IgA antibodies are both conjugated to the same second fluorochrome. In yet another embodiment, the antibodies against IgE and IgA are both conjugated to the same first fluorochrome, and the IgE and IgG antibodies are both conjugated to the same second fluorochrome. Preferably, the fluorochrome used for the anti-IgE is not conjugated to any other reagent in order to achieve an optimal separation of the IgE expressing B cells. It may be useful to include in the panel of fluorochrome-conjugated antibodies used in step (i) at least one further antibody reactive with a B cell antigen. For example, the further antibody is reactive with a marker for characterization of memory B cells, preferably a marker selected from the group consisting of CD23, CD40, CD80, CD86, CD180, TACI, CD200, CD73 and CD62L. TCL1 is suitably used for intracellular staining and discrimination between immature/naive versus memory B cells or for exclusion of Fcepsilon-RII/CD23+ B-cells (e.g. CD23) that may binding IgE and appear as non-specifically stained IgE+ naive B-cells. The panel may also comprise one or more antibodies useful for the characterization of plasma B cells, for example an antibody against the CD20 or CD138 antigen.

Following sample staining, the sample is subjected to multi-color (e.g. 8 or >8 color) flow cytometry and gated for lymphocytes based on the forward scatter and side scatter pattern, typically followed by exclusion of cell doublets and multiplets in a e.g. forward scatter-pulse area versus forward scatter pulse-height bivariate dot plot, according to conventional criteria. See the dot plots on the left hand side of exemplary gating strategies shown in FIG. 1. Alternatively, B-cells can be specifically gated on CD19 versus side scatter, and further subsetted into $CD38^{dim}$ memory B cells and $CD38^{hi}$ plasma cells. The gated lymphocytes are subsequently gated for expression of the B cell specific marker (e.g. CD19) and CD38 antigen to discriminate between $CD38^{dim}$ memory B cells and $CD38^{hi}$ plasma cells. See the second dot plot in each of the panels of FIG. 1. As used herein, the term "$CD38^{dim}$" is meant to refer to those cells showing diminished CD38 expression. It may also be denoted as the "CD38±" or "CD38low" cell population. As used herein, the term "$CD38^{hi}$" is meant to refer to those cells showing high CD38 expression. It may also be denoted as the "CD38++" cell population.

Following the identification of the memory B cell population and/or the plasma cell population, the IgE positive cells in these population(s) are detected and quantitated. This is done by the negative selection of cells expressing IgM, IgA, IgG and/or IgD and the positive selection of IgE expressing cells. It was found that this bidirectional approach is necessary and sufficient for an accurate detection of low numbers of IgE+ B cells. Preferably, the negative selection comprises exclusion of at least two, preferably at least three, most preferably all isotypes other than IgE. As is illustrated in FIG. 1, various gating strategies can be used to achieve this. In one embodiment, selections are made for IgM–IgD– cells, followed by selection of IgA–IgG– cells. Within the resulting cell population, IgE+ cells are selected. See panel A of FIG. 1. In another embodiment, IgM–IgD– cells are selected followed by the identification of IgE positive cells in a combined staining for IgE+IgA and IgG+IgA. See panels B and C of FIG. 1. The skilled person will be able to design variant gating strategies aiming at a similar result. A method of the invention typically comprises a positive selection step for IgE-expressing plasma cells and B cells preceded by the exclusion of cells that express one of the other Ig isotypes, preferably by exclusion of cells expressing IgM, IgD, IgG, IgA. However, it is also possible to directly gate on the IgE expressing cells and subsequently "clean" the IgE+ cells from cells expressing other isotypes.

For many diagnostic or classification purposes, it can be advantageous to further characterize the IgE+ memory B cell population and/or the plasma cell population.

For example, the characterization may comprise staining the cells with a fluorochrome-conjugated antibody against CD27 and detecting within the IgE+ memory B cell population the CD27+ and CD27− memory B cell subsets to distinguish between CD27+IgE+ and CD27−IgE+ subsets that in healthy individuals have undergone either a germinal center-dependent or independent response, respectively. Preferably, staining for CD27 is performed simultaneously with staining for the Ig isotypes, the B cell marker and CD38, i.e. the anti-CD27 antibody is preferably comprised in the antibody panel used in step (i) of the method. The distinction between CD27+ and CD27− subsets of the population of IgE-expressing memory B cells can be readily performed as the last stage of the gating strategy. See for example the right hand side dot plots of panels A en B of FIG. 1.

As is described herein below, it was found that blood samples obtained from atopic dermatitis (AD) patients contained increased numbers of IgE+ memory B cells, and that these cells mainly concerned CD27− cells. Importantly, increased IgE+ memory B cell numbers in AD patients were not correlated with increased serum IgE levels, which have thus far been used as prime diagnostic parameter. Serum IgE levels do not seem to correlate with disease activity or severity, which might be caused by the fact that most secreted IgE is bound to the IgE high affinity receptor FcεRI on mast cells and basophils.

In an alternative embodiment, the further characterization comprises determining the antigen specificity of the IgE+ memory B cell population and/or the plasma cell population by contacting the cells with a fluorochrome-conjugated antigen of interest. It will be understood that the fluorochrome selected for conjugation to the antigen is distinct from those conjugated to the antibodies used. In a preferred embodiment, the antigen is an allergen or an antigenic fragment thereof. The term "allergen" refers to any naturally occurring protein or mixtures of proteins or chemicals/drugs that have been reported to induce allergic, i.e. IgE-mediated reactions upon their repeated exposure to an individual. The allergen may be a naturally occurring allergen or a chemical/drug. Examples of naturally occurring allergens include pollen allergens (e.g. tree, weed, herb and grass pollen allergens), mite allergens (from e.g. house dust mites and storage mites), insect allergens (e.g. inhalant, saliva- and venom origin allergens), animal allergens from e.g. saliva, hair and dander from e.g. dog, cat, horse, rat, mouse, etc. fungi allergens and food allergens (from e.g. peanut, shrimp and fish). The allergen may be a modified allergen or a recombinant allergen or a recombinant mutant allergen, any allergen fragment e.g. a fragment above about 10 amino acids or any combination thereof; in addition, it can also be a chemical or a drug administered systemically or locally to an individual. Cells can be stained with the fluorochrome-conjugated antigen (allergen) following isolation of the cell population of interest. However, for practical reasons the staining for antigen (allergen) specific IgE antibodies is advantageously performed during step (i) of the method of the invention.

In a further embodiment of a method of the invention, characterization of IgE+ cells comprises the step of isolating IgE+ memory B cell subsets and subjecting the isolated subsets to a molecular analysis of their replication history, somatic hypermutation (SHM) and/or class switch recombination (CSR) profiles by a method known in the art. Such molecular analysis can provide valuable information for the classification of a disease. For example, CD27+ and CD27− subsets can be obtained and their replication history is determined e.g. by the analysis of coding joint/signal joint ratio or IGK-deleting rearrangements. SHM can for instance be determined by analysis of IGH gene rearrangements and/or the frequency of mutated IGK alleles. It was found that CD27+IgE+ memory B cells had a high replication history of about 10 cell cycles accompanied by moderately high SHM loads in IGHV genes and a high frequency of mutated IGKV3-20 alleles, whereas CD27−IgE+ memory B cells showed a low replication history of about 4 cell cycles, accompanied by high SHM loads in IGHV genes and low frequencies of mutated IGKV3-20 alleles (FIG. 3).

It will be understood that a method of the invention finds several important applications, in particular in the field of medical diagnostics of humans and animals. Provided herein is a method to diagnose and/or classify a disease or condition associated with altered (production of) IgE levels and/or IgE specificity, comprising quantitating IgE+ memory B cell and/or plasma cell subsets in a biological sample isolated from a mammalian subject according to a method of the invention, further comprising the step of correlating the amount of IgE+ memory B cells and/or IgE+ plasma cells with disease diagnosis and/or classification, wherein an increased number of IgE+ memory B cells and/or IgE+ plasma cells as compared to healthy controls, or a another sample from the same subject, is indicative of the subject suffering from the disease. For example, an amount at least 1.2 IgE+ memory B cells per microliter blood is indicative of a human subject suffering from atopic dermatitis. Quantitation may advantageously be accompanied by further characterization of the IgE+ B cells, preferably by one or more of the method steps disclosed herein above. The method can be used to diagnose and/or classify any IgE-mediated disease.

Exemplary diseases include type I hypersensitivity, preferably selected from asthma, hay fever (rhinitis), food allergy, atopic dermatitis, an immune disease with suspected involvement of IgE antibodies, for example rheumatoid arthritis (RA), Graves disease or SLE. In one embodiment, it is hyper IgE syndrome (HIES). HIES is a rare primary immunodeficiency disease most commonly characterized by a triad of findings, including increased serum IgE levels, recurrent skin abscesses, and pneumonias leading to pneumatocele formation. HIES can be caused by genetic defects in the DOCKS, TYK2 or STAT3 genes.

Alternatively, the disease is a parasitic infection, for example helminth infection. Infections with helminth parasites e.g. *Heligmosomoides polygyrus, Trichuris muris* or *Schistosoma mansoni*, are associated with an IgE isotype switch and high serum IgE concentrations. IgE is rapidly bound by the high affinity IgE receptor (FcεRI), thereby sensitizing FcεRI-bearing basophils and mast cells for IgE-inducible effector functions such as IL-4 production. A method of the invention can be used to diagnose and follow IgE-mediated infections.

Also provided herein is the use of the IgE+ memory B cell and/or IgE+ plasma cell number as a disease marker for type I hypersensitivity and diseases related thereto, as well as a method for diagnosing type I hypersensitivity in a subject, comprising determining the number of IgE+ memory B cells and/or IgE+ plasma cells in a sample obtained from the subject.

A further advantageous application of the concept underlying the invention resides in therapy monitoring. For instance, the (early) monitoring of treatment efficacy of anti-IgE therapy or allergen-specific immunotherapy (oral/subcutaneous).

Humanized anti-IgE monoclonal antibodies with very particular binding specificities were found effective in neutralizing free IgE and inhibiting IgE production by B cells. Omalizumab is a recombinant DNA-derived humanized IgG1k monoclonal antibody that selectively binds to human IgE. Omalizumab (trade name Xolair, Genentech/Novartis) is a humanized antibody drug, approved for patients with moderate-to-severe or severe allergic asthma, which is caused by hypersensitivity reactions to certain harmless environmental substances. Xolair is intended for long-term treatment. Clinical trials have demonstrated that it takes at least 12-16 weeks for Xolair treatment to show effectiveness. At 16 weeks after commencing Xolair therapy, patients should be assessed by their physician for treatment effectiveness before further injections are administered. The decision to continue Xolair following the 16-week timepoint, or on subsequent occasions, should be based on whether a marked improvement in overall asthma control is seen.

Heretofore, it was not feasible to reliably detect and quantitate IgE-expressing B cells. With the development of the flow-cytometric based procedure described herein above, the invention also provides a method for early monitoring of the effectiveness of anti-IgE therapy, comprising analyzing memory B cell and plasma cell subsets in a biological sample isolated from a subject receiving anti-IgE therapy using the approach for detecting IgE+ B cells as disclosed herein, further comprising the step of correlating the amount of IgE+ memory B cells and/or IgE+ plasma cells with the disease diagnosis and/or classification, wherein a reduction in the number of (allergen-specific) IgE+ memory B cells and/or IgE+ plasma cells as compared to pre-treatment values is indicative of the treatment being successful. The information obtained can be of help for the clinician to decide on therapy continuation, and on adjusting the appropriate dose and frequency of antibody administration.

In a specific aspect, the invention provides a method for monitoring the efficacy of treating a human adult or child with a humanized antibody against IgE, preferably wherein the antibody is omalizumab or a functional homolog thereof. In one embodiment, the functional homolog is a chimeric monoclonal antibody. It may bind specifically to the Cepsilon3 domain of IgE, the site of high-affinity IgE receptor binding. In one embodiment, the antibody is Tanox product CGP 51901. In another embodiment, the anti-IgE antibody is the humanized 47H4 clone, which targets the extracellular (membrane proximal) M1' domain of human membrane-bound IgE molecules. The advantage of this antibody is that it does not recognize serum IgE, implying that serum IgE molecules will not "consume" the 47H4 anti-IgE antibody. Crosslinking of membrane IgE molecules by the 47H4 antibody clone triggers apoptosis of the IgE expressing B cells (Brightbill et al J Clin Invest 2010, 120:2218-2229).

The anti-IgE therapy may involve antibody treatment in combination with one or more other drugs such as corticosteroids.

A further advantageous aspect of the invention relates to monitoring of the efficacy of allergen-specific immunotherapy. Allergen-specific immunotherapy (also termed hyposensitization therapy, immunologic desensitization, hyposensibilization, or allergen immunotherapy) is a form of immunotherapy for allergic disorders in which the patient is vaccinated with increasingly larger doses of an allergen with the aim of inducing immunologic tolerance. Allergen specific immunotherapy is the only treatment strategy which treats the underlying cause of the allergic disorder. It can either reduce the need for medication, severity of symptoms or eliminate hypersensitivity altogether. Allergen can be administered under the tongue (sublingually) or by injections under the skin (subcutaneous).

The immune system of allergy affected individuals, for reasons not fully understood, misinterprets a usually innocuous substance as a disease agent and begins producing IgE. This is called the 'primary antibody response.' The IgE produced during this response binds to basophils in the bloodstream and to a similar type of cell called mast cells in the tissues. When the person again encounters the allergen, these basophils and mast cells that have bound to IgE release histamine, prostaglandins, and leukotrienes, which causes inflammation of the surrounding tissues, resulting in allergic symptoms. Immunotherapy via repeated exposure to a specific allergen via either sublingual or subcutaneous route leads to a desensitisation to the allergen and thus a reduction in allergic symptomatology and use of symptomatic based treatments. The exact mechanism is not fully understood but it is accepted that immunotherapy causes modification of the immune system. This modification leads to changes in IgE synthesis and the production of IgE blocking antibodies which thus reduces the immune systems allergic response to specific allergens. There is also a shift from Th2 responses towards regulatory T cells. The molecular mechanism of such immunotherapy can be partly interpreted as that there occurs induction of allergen-specific IgG to neutralize the allergen instead of induction of allergen-specific IgE.

As will be appreciated by the skilled person, a method of the present invention is highly suitable to monitor any quantitative changes in allergen-specific B cells in a biological sample of a patient suffering from an allergy and receiving allergen-specific immunotherapy. To that end, the IgE-expressing cells (be it memory B cells and/or plasma cells) are easily identified and quantitated by staining with the allergen of interest, the allergen being provided with a detectable label like a fluorochrome. Accordingly, provided is a method for the (early) monitoring of treatment efficacy of allergen-specific immunotherapy The method comprises analyzing memory B cell and plasma cell subsets in a biological sample isolated from a subject receiving said immunotherapy (oral/subcutaneous) using a procedure as described herein above for detecting IgE+ memory B cells and/or IgE+ plasma cells. The procedure includes determining the allergen specificity of the IgE+ memory B cell population and/or the IgE+ plasma cell population by contacting the cells with a fluorochrome-conjugated allergen of interest and further comprises the step of correlating the amount of IgE+ memory B cells and/or IgE+ plasma cells with the disease diagnosis and/or classification, wherein a reduction in the number of allergen-specific IgE+ memory B cells and/or IgE+ plasma cells as compared to pre-treatment values is indicative of the treatment being successful.

In a specific aspect, the method is used to monitor the efficacy of immunotherapy for allergy against an allergen selected from the group consisting of pollen allergens (e.g. tree, weed, herb and grass pollen allergens), mite allergens (from e.g. house dust mites and storage mites), insect allergens (e.g. inhalant, saliva- and venom origin allergens), animal allergens from e.g. saliva, hair and dander from e.g. dog, cat, horse, rat, mouse, etc. fungi allergens, drug/chemical allergens and food allergens, e.g peanut, shrimp, fish etc.

A still further aspect of the invention relates to a diagnostic kit comprising reagents for performing a method herein disclosed. In one embodiment, it is a diagnostic assay kit e.g. to diagnose and/or classify and/or monitor treatment efficacy of a disease or condition associated with altered (production of) IgE levels and/or IgE specificity. The kit comprises a panel of fluorochrome-conjugated antibodies against IgM, IgA, IgG, IgD and IgE; an antibody against a B cell marker and an antibody against the CD38 antigen. Preferably, the B cell marker is CD19, CD20, CD79a or CD22 antigen, more preferably CD19 antigen. For reasons explained above, the kit preferably also contains a fluorochrome-conjugated anti-CD27 antibody. Each antibody may be conjugated to a distinct fluorochrome to allow for distinct detection by flow-cytometry. However, it is also possible to use a single fluorochrome for two distinct antibodies, for example, two antibodies selected from the group consisting of anti-IgE, anti-IgA and anti-IgG may be conjugated to the same fluorochrome, preferably wherein the fluorochrome is FITC or PE. In one embodiment, the antibodies against IgE and IgA are both conjugated to the same first fluorochrome, and the IgA and IgG antibodies are both conjugated to the same second fluorochrome.

The kit may further comprise one further fluorochrome-conjugated antibody reactive with a B cell antigen. Preferably, the further antibody is reactive with a marker for characterization of memory B cells and/or plasma cells. For example, the kit also comprises one or more antibodies against a marker selected from the group consisting of CD23, CD40, CD80, CD86, CD180, TACI, CD200, CD73, TCL1 and CD62L. The kit may also comprise one or more antibodies useful for the characterization of plasma cells, for example an antibody against the CD20 or CD138 antigen. As will be understood, any fluorochrome suitable for detection by flow cytometry may be used. Exemplary antibody panels are shown in Table 1 herein below. The skilled person will understand that many variations are possible with respect to fluorochrome selection and combination to allow for simultaneous detection of the antibodies.

A diagnostic kit of the invention may further contain a reagent to detect antigen-specific IgE expressing B cells (IgE+ memory B cells and IgE+ plasma cells). For example, the reagent is an antigen of interest conjugated to a detectable label, preferably a fluorochrome. In a specific embodiment, the kit is a diagnostic assay kit to monitor treatment efficacy of allergen-specific immunotherapy. In addition to the reagents mentioned above, the kit preferably comprises at least one fluorochrome-conjugated allergen of interest or antigenic fragments thereof. An allergen is any naturally occurring protein that can induce allergic, i.e. IgE-mediated reactions upon their repeated exposure to an individual. The labelled allergen may a naturally occurring allergen. Examples of naturally occurring allergens include pollen allergens (e.g. tree, weed, herb and grass pollen allergens), mite allergens (from e.g. house dust mites and storage mites), insect allergens (e.g. inhalant, saliva- and venom origin allergens), animal allergens from e.g. saliva, hair and dander from e.g. dog, cat, horse, rat, mouse, etc. fungi allergens, drug/chemical allergens and food allergens. The allergen may be a modified allergen or a recombinant allergen or a recombinant mutant allergen, any allergen fragment e.g. a fragment of at least 8 amino acids or any combination thereof.

The kit may further comprise any additional reagent, buffer, or device for use in a method of the invention. For example, it may contain reagents to prepare a standard curve, to calibrate the flow cytometer, positive controls, negative controls, and the like.

BRIEF DESCRIPTION OF THE DRAWINGS

FIG. 3. Molecular characteristics of IgE+ memory B cells.

FIG. 4. IgE memory B cells are present in patients with CD40L deficiency. Flow cytometric analysis of blood samples from a healthy control (A) and a patient with CD40L deficiency (B). Gating strategy is similar to FIG. 1B.

EXPERIMENTAL SECTION

Figure 1C:
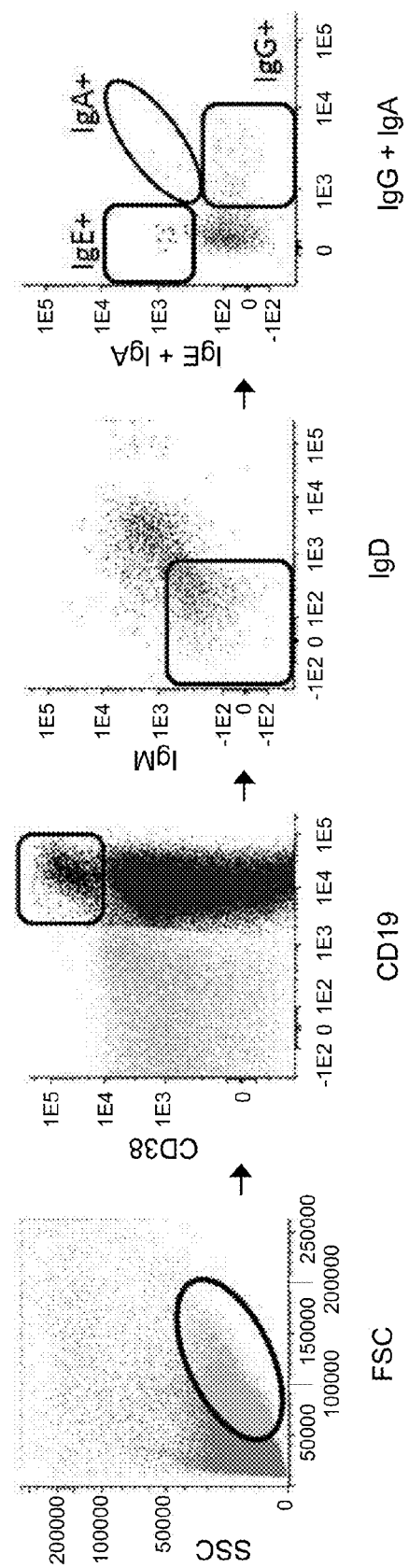
FIG. 1. Gating strategies for analysis of CD27+IgE+ and CD27-IgE+ memory B cell subsets and IgE+ plasma cells. (A) First, lymphocytes are gated based on forward scatter and side scatter patterns. Subsequently, CD19+CD38$^{dim}$ B lymphocytes are gated, and selections are made for IgM−IgD− B cells, followed by IgA−IgG− B cells. Within these events, IgE+ B cells are defined and split based on CD27 expression. (B) Similar selection criteria are applied as in (A) to obtain IgM−IgD− B cells. Subsequently, IgE positive B cells are selected in a combined staining for IgE+IgA and IgG+IgA. The IgE+ cells are then subdivided into CD27+ and CD27− subsets. (C) Gating strategy for the detection of IgE+ plasma cells in tonsil with the same flow cytometric approach as in (B). Following selection of live lymphocytes, CD19+CD38hi plasma cells are gated. From these, the IgM−IgD− fraction was studied for IgA, IgG and IgE expression.

The present inventors postulate that, following specific immune responses, IgE+ memory B cells and IgE+ plasma cells are formed, such cells becoming detectable in lymphoid tissues and in peripheral blood. IgE+ memory B cells and IgE+ plasma cells are present in low numbers and have therefore not been reliably detected before. Herein a flow cytometric approach was developed to reliably detect IgE+ plasma cells and two IgE+ memory B subsets in blood and lymphoid tissues. Upon exclusion of plasma cells and B cells that express other Ig isotypes (IgM, IgD, IgG, IgA), IgE+CD38hiCD27+ plasma cells can be detected within the plasma cell compartment, at the same time both CD27+IgE+ and CD27−IgE+ memory B cell subsets can be detected within the CD38dim B cell fraction. In addition, CD23+ (low affinity IgE receptor II/FcepsilonRII) B-cells may also be specifically excluded to avoid non-specific identification of these cells as false-IgE+ lymphocytes.

Biological samples from healthy children and adult controls as well as patients with atopic dermatitis were analyzed according to a method of the invention to quantify CD27−IgE+ and CD27+IgE+ memory B cell subsets. Additionally, both populations from healthy donors were purified using high-speed fluorescence activated cell sorting (FACS) and subjected for further characterization by performing molecular analysis of their replication history, SHM and CSR profiles, to determine their origin and maturation pathways.

Materials and Methods
Blood Samples

Tonsil samples were collected from otherwise healthy children who underwent tonsillectomy at the Erasmus MC— Sophia Children's Hospital. Blood samples were collected from healthy children and adults, and from patients with atopic eczema/dermatitis who visited the Dermatology clinic of the Erasmus MC, Rotterdam, the Netherlands after informed consent was given by the children and their parents and the participating adult volunteers.

Flow Cytometric Immunophenotyping and High-Speed Cell Sorting

Following bulk lysis with $NH_4Cl$, blood leukocytes were incubated at room temperature for 10 minutes with monoclonal antibodies for identification and characterization of the various B cell subsets. Subsequently, the cells were washed and analyzed on a LSR II or FACSCanto II (BD Biosciences).

Blood B cells were isolated from buffy coat post-ficoll mononuclear cells by magnetic separation with CD19 beads (Miltenyi Biotech). From these, two naive and 8 memory B cell subsets were purified on a FACSAria cell sorter (BD Biosciences). For optimal purification, we included antibodies against all five Ig isotypes (IgM, IgD, IgA, IgG and IgE) in separate fluorescence channels. Additionally, we were able to limit these to four channels. Since the expression of IgG, IgA or IgE on B cells is mutually exclusive, we introduced two of each 3 antibodies in two channels (Table 1). A similar flow cytometric analysis approach was applied on single cell suspensions of tonsil samples to detect IgE+ plasma cells.

List of Antibodies Used:

| Antibody | Fluorochrome | Clone | Supplier | Cat no |
| --- | --- | --- | --- | --- |
| IgM | Horizon V450 | G20-127 | BD Biosciences | Custom conjugate |
| IgD | Biotin + Streptavidin PO | IA6-2 | BD Biosciences + Invitrogen | 555777 + S32365 |
| IgE | FITC | | Invitrogen | H15701 |
| IgA | FITC | IS11-8E10 | Miltenyi | 130-93-071 |
| IgA | PE | IS11-8E10 | Miltenyi | 130-93-128 |
| IgG | PE | G18-145 | BD Biosciences | 555787 |
| CD19 | PerCP-Cy5.5 | SJ25C1 | BD Biosciences | 332780 |
| CD19 | PE-Cy7 | SJ25C1 | BD Biosciences | 341113 |
| CD20 | PerCP | L27 | BD Biosciences | 347674 |
| CD20 | PE-Cy7 | L27 | BD Biosciences | 335828 |
| CD27 | PerCP-Cy5.5 | L128 | BD Biosciences | 649805 |
| CD27 | APC | L128 | BD Biosciences | 337169 |
| CD38 | APC-H7 | HB7 | BD Biosciences | 646786 |
| CD200 | APC | OX104 | e-Bioscience | 17-9200-42 |
| CD200 | PE-Cy7 | OX104 | e-Bioscience | 25-9200-42 |

TABLE 1

Exemplary Antibody panels for 8-color flow cytometric analysis of IgE expressing B cells

| PB/V450 | PO/V500 | FITC | PE | PerCP | PE-Cy7 | APC | APC-H7 |
| --- | --- | --- | --- | --- | --- | --- | --- |
| IgM | IgD-bio | IgA | IgG | CD27 | CD19 * | IgE | CD38 |
| IgM | IgD-bio | IgG | IgA | CD27 | CD19 * | IgE | CD38 |
| IgM | IgD-bio | IgE + IgA | IgG + IgA | CD27 | CD19 * | extra** | CD38 |
| IgM | IgD-bio | IgG + IgA | IgE + IgA | CD27 | CD19 * | extra** | CD38 |
| IgM | IgD-bio | IgE + IgG | IgA + IgG | CD27 | CD19 * | extra** | CD38 |
| IgM | IgD-bio | IgA + IgG | IgE + IgG | CD27 | CD19 * | extra** | CD38 |
| IgM | IgD-bio | IgA + IgE | IgG + IgE | CD27 | CD19 * | extra** | CD38 |
| IgM | IgD-bio | IgG + IgE | IgA + IgE | CD27 | CD19 * | extra** | CD38 |
| IgM | IgD-bio | IgE | IgG + IgA | CD27 | CD19 * | extra** | CD38 |
| IgM | IgD-bio | IgG + IgA | IgE | CD27 | CD19 * | extra** | CD38 |
| IgM | IgD-bio | IgE + IgA | IgG + IgA | CD19 | extra** | CD27 | CD38 |
| IgM | IgD-bio | IgE + IgA | IgG + IgA | extra** | CD19 | CD27 | CD38 |
| IgM | IgD-bio | IgE + IgA | IgG + IgA | CD19 | CD38 | CD27 | — |

TABLE 1-continued

Exemplary Antibody panels for 8-color flow cytometric analysis of IgE expressing B cells

| PB/V450 | PO/V500 | FITC | PE | PerCP | PE-Cy7 | APC | APC-H7 |
|---|---|---|---|---|---|---|---|
| IgM | IgD-bio | IgE + IgA | IgG + IgA | extra** | CD20 | CD27 | CD38 |
| IgM | IgD-bio | IgE + IgA | IgG + IgA | CD20 | extra** | CD27 | CD38 |

* CD19 can be replaced by another pan-B cell marker such as CD20, CD79a or CD22
**This position is open for an additional marker. Preferred markers are CD80, CD180, TACI, CD200, CD73 and CD62L for further characterization of memory B cells. TCL1 can also be used for intracellular staining and discrimination between immature/naïve versus memory B-cells; CD23 can also be used to exclude FcepsilonRII+ B cells. The additional marker can also be a fluorochrome-conjugated allergen or allergen fragment.

Sequence Analysis of Complete IGH Gene Rearrangements

DNA was isolated from each sorted subset with the GenElute Mammalian Total DNA Miniprep Kit and RNA was isolated from Ig-class switched B cell subsets using the GeneElute Mammalian Total RNA Miniprep Kit (Sigma-Aldrich). Complete IGH gene rearrangements were amplified from the genomic DNA of IgM+B cell subsets using 6 VH-FR1 forward primers and one JH consensus reverse primer (Van Dongen et al. 2003. Leukemia 17:2257-2317.21). After reverse transcription using random hexamers, IGHA, IGHG and IGHE transcripts were amplified using the same six IGHV-FR1 forward primers in combination with an IGHA (5'-GTGGCATGTCACGGACTTG-3')(SEQ ID NO; 1), an IGHG (5'-CACGCTGCT-GAGGGAGTAG-3')(SEQ ID NO; 2) consensus reverse primer, or with two IGHE reverse primers (5'-CATCACCG-GCTCCGGGAAGTAGCC-3' (SEQ ID NO: 3) and 5'-GTTTTTGCAGCAGCGGGTCAAG-3')(SEQ ID NO; 4) in a semi-nested approach. All PCR products were cloned into pGEM-T easy vector (Promega, Madison, Wis.) and prepared for sequencing on the ABI Prism 3130 XL fluorescent sequencer (Applied Biosystems). Obtained sequences were analyzed with the IMGT database (http://imgt.cines.fr/) to assign the IGHV, IGHD and IGHJ genes, and to identify somatic mutations (Lefranc et al. 2009. Nucleic Acids Res 37:D1006-1012.22). From each unique clone, the mutation frequency was determined within the IGHV gene, as was the length and composition of the IGH-CDR3.

Replication History Analysis Using the KREC Assay

The replication history of sorted B cell subsets was determined with the Kappa-deleting Recombination Excision Circles (KREC) assay as described previously. Briefly, the amounts of coding and signal joints of the IGK-deleting rearrangement were measured by RQ-PCR in DNA from sorted B cell populations on an ABI Prism 7000 (Applied Biosystems). Signal joints, but not coding joints are diluted two-fold with every cell division. To measure the number of cell divisions undergone by each population, we calculated the ratio between the number of coding joints and signal joints. The previously established U698 DB01 (InVivoScribe) control cell line contains one coding and one signal joint per genome and was used to correct for minor differences in efficiency of both RQ-PCR assays (van Zelm et al. 2007 J Exp Med 204:645-655).

Ig κREHMA

The frequency of mutated IGK alleles was determined with the Igκ restriction enzyme hot-spot mutation assay (IgκREHMA) as described previously (van Zelm, M. C. et al. 2007; Andersen, P. et al. 2005. Blood 105:511-517). Briefly, PCR was performed on genomic DNA using a HEX-coupled Vκ3-20 intron forward primer and two FAM-coupled IGKJ reverse primers recognizing all five IGKJ gene segments. The PCR products were digested by the KpnI and Fnu4HI restriction enzymes and run on the ABI Prism 3130 XL. Fnu4HI recognizes two adjacent sites in the unmutated gene product in the hot-spot region of VK-CDR1. Unmutated gene products can therefore be visualized as 244 or 247-bp HEX-coupled fragments. KpnI cuts the gene product in FR2 downstream of the Fnu4HI sites, resulting in a 262-bp HEX-coupled mutated fragment. The unmutated B cell line CLL-1 was used as a positive control for complete digestion with Fnu4HI. The digests hardly contained undigested gene products of 481 bp, indicating complete digestion by KpnI.

Statistical Analyses

Statistical analyses were performed with the Mann-Whitney U test, or $X^2$ test as indicated in detail in the Figure legends. p values <0.05 were considered statistically significant.

Results

Reliable Detection of IgE+ Memory B Cells and Plasma Cells in Healthy Individuals Multi-color flow cytometry is a powerful technique to identify multiple subsets within a cell lineage. We designed a new 8-color flow cytometric analysis with CD19 and CD38 antibodies to detect mature B-lymphocytes and plasma cells (Table 1 and FIG. 1). Furthermore, all antibodies against all 5 Ig isotypes (IgA, IgD, IgE, IgG and IgM) were included. For accurate detection of low numbers of IgE+ B cells, it was found to be crucial to exclude B cells that express other Ig isotypes (IgM, IgD, IgA ang IgG; FIG. 1A). Thus, we identified IgE-expressing plasma cells within the CD38hiCD27+ fraction and two IgE+ memory B cells that were CD38dim and either CD27+ or CD27–. These 8 markers can be used in 8-color flow cytometry, but do not allow for inclusion of additional markers, thus flow cytometer instruments with the ability to measure more than 8-colors being required for this purpose.

To free one fluorochrome position for an additional marker, we combined three markers in two channels (FIG. 1B). Because each B cell can only express a receptor of the IgA, IgE or IgG isotype, we combined these three antibodies in two channels: IgA and IgE in FITC, and IgE and IgG in PE. Thus, Single FITC+ B cells will be IgE+, single PE+ B-cells IgG+ and FITC+PE+ will be IgA+. Naturally, other combinations of these three isotypes are also possible (Table I). Subsequently, we included CD27 and CD38 to separate IgE-expressing plasma cells from memory B cells, since these are functionally distinct. Finally, CD27+ memory B cells and CD27– memory B cells were separated, because these are derived from distinct maturation pathways.

To reliably detect IgE+ B cells, we excluded expression of one of the other Ig isotypes (IgA, IgD, IgG and IgM). Subsequently, we divided IgE+ B lymphocytes into CD27+ and CD27– subsets (FIG. 1). To confirm that the cells detected with this approach corresponded to memory B cells, we analyzed them for expression of CD80, CD180 and TACI. Similar to other memory B cell subsets, IgE+ memory B cells showed upregulation of these surface proteins as compared with naive B cells thus confirming their memory B cell phenotype. Other preferential markers to include in 8-color (or even >8 color) flow cytometry are CyTCL1, CD200, CD73, CD23 and CD62.

Peripheral blood contains very few circulating plasma cells, in contrast to peripheral lymphoid tissue. Therefore, we studied the presence of IgE+ plasma cells in single cell suspensions of childhood tonsils. Following gating on live cells, CD38hi plasma cells that were IgM−IgD−, we were able to detect IgE+ plasma cells (FIG. 1C). Thus, our flow cytometric approach enables the detection and quantification of IgE+ memory B cells and plasma cells in blood and peripheral lymphoid tissues.

Quantification of IgE+ Memory B Cells Subsets in Blood of Healthy Individuals

Figure 2:
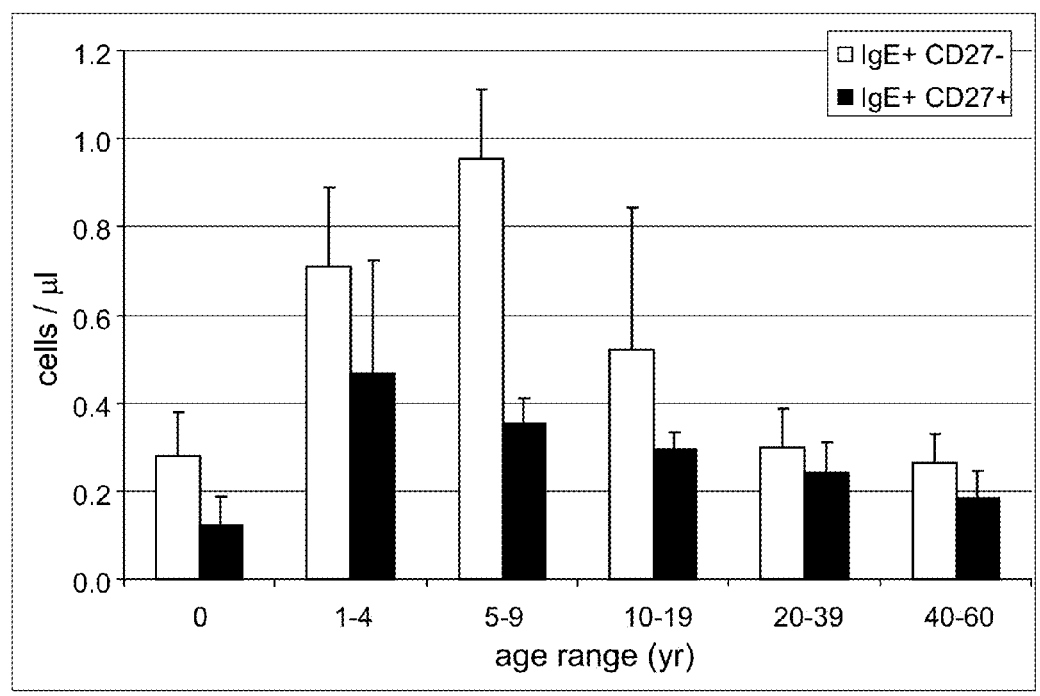
FIG. 2. Absolute cell numbers of IgE+ memory B cells in neonatal cord blood (0 yr), healthy children (1-4 yr, 5-9 yr and 10-19 yr) and adults (20-39 yr and 40-60 yr). The bars depict the mean number of cells per microliter blood for CD27-IgE+ and CD27+IgE+ memory B cells with SEM.
Figure 3A:
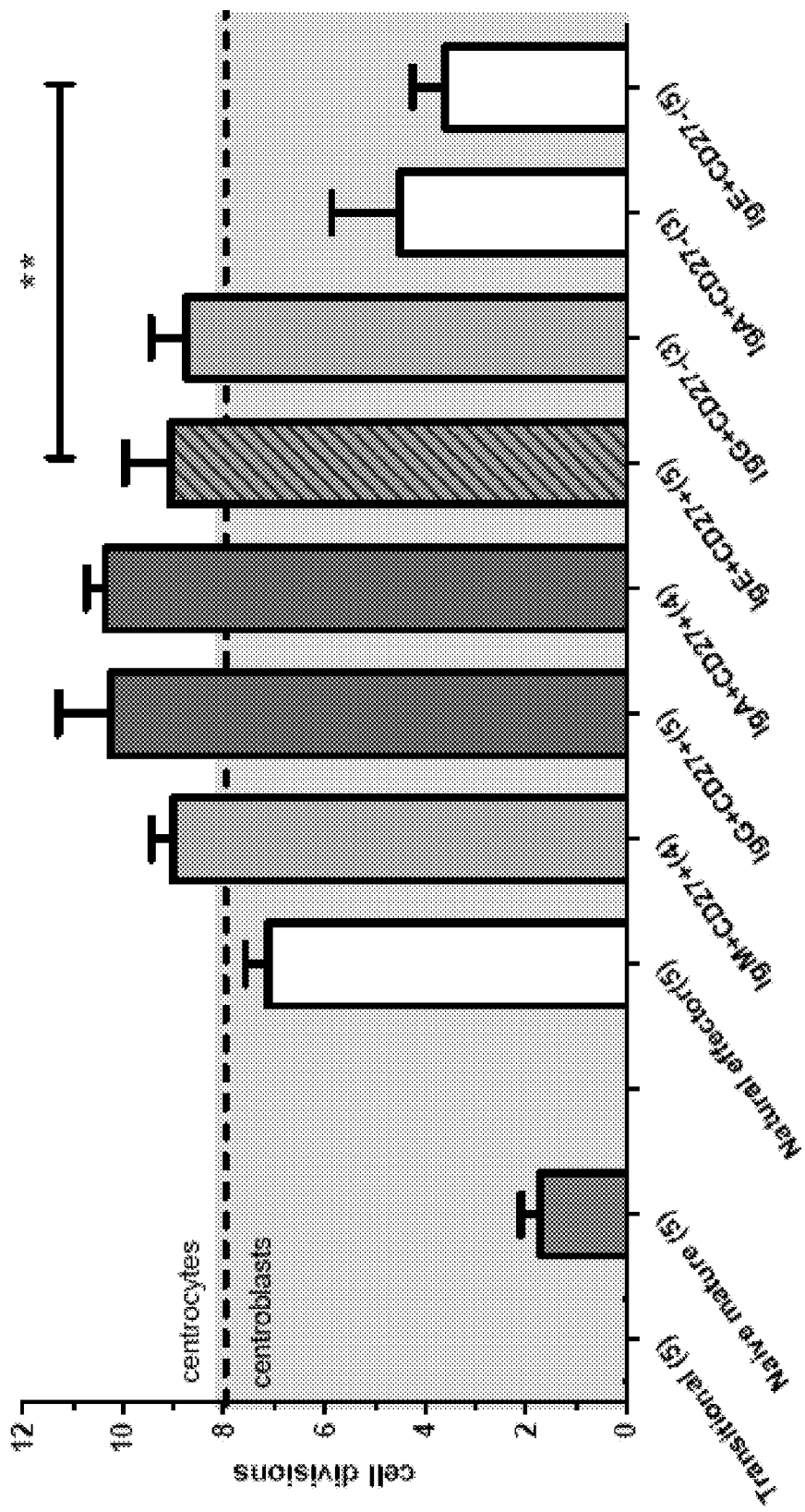
FIG. 3A: cell division.
Figure 3B:
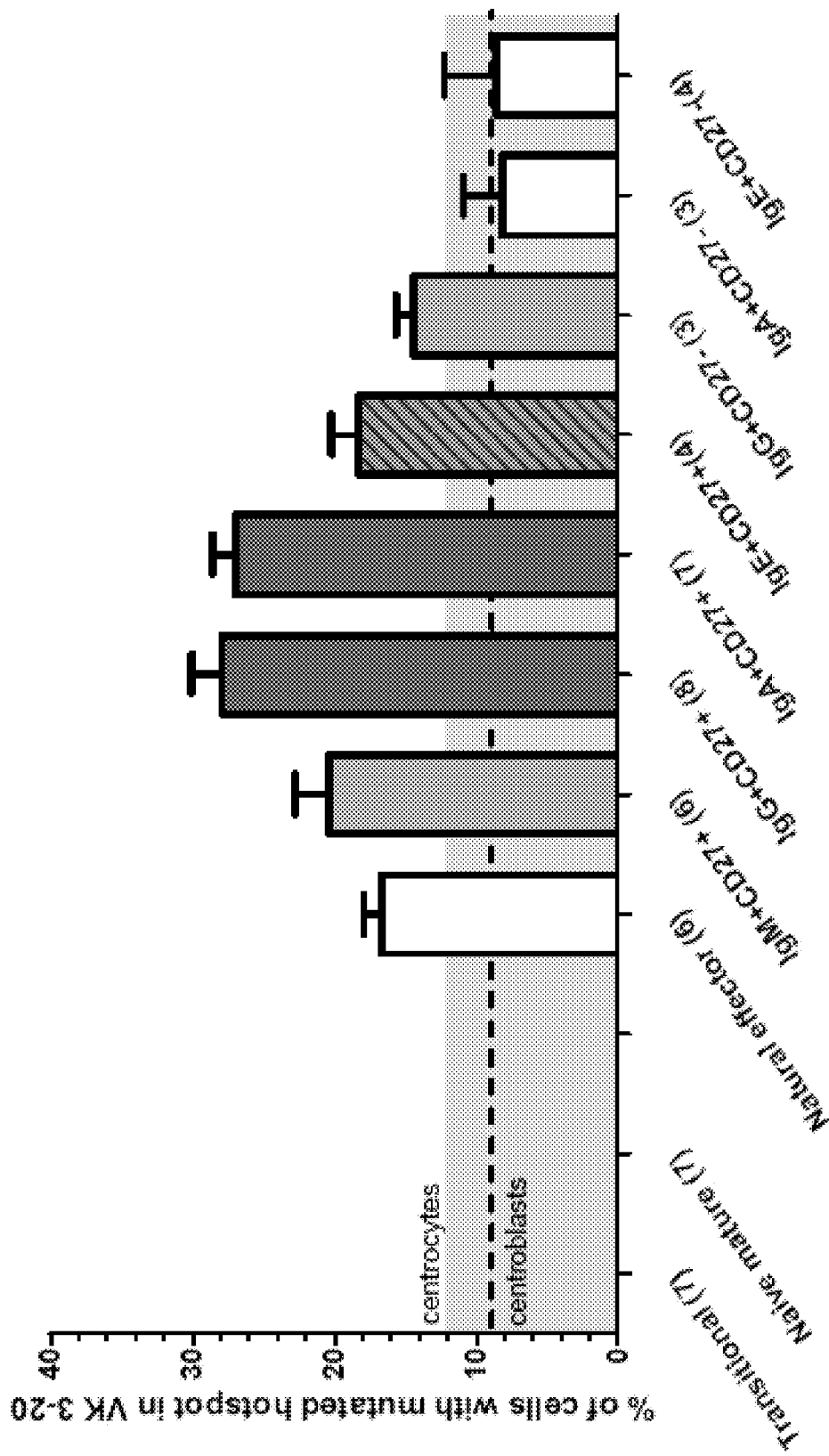
FIG. 3B: mutated hotspot in Vκ 3-20.
Figure 3C:
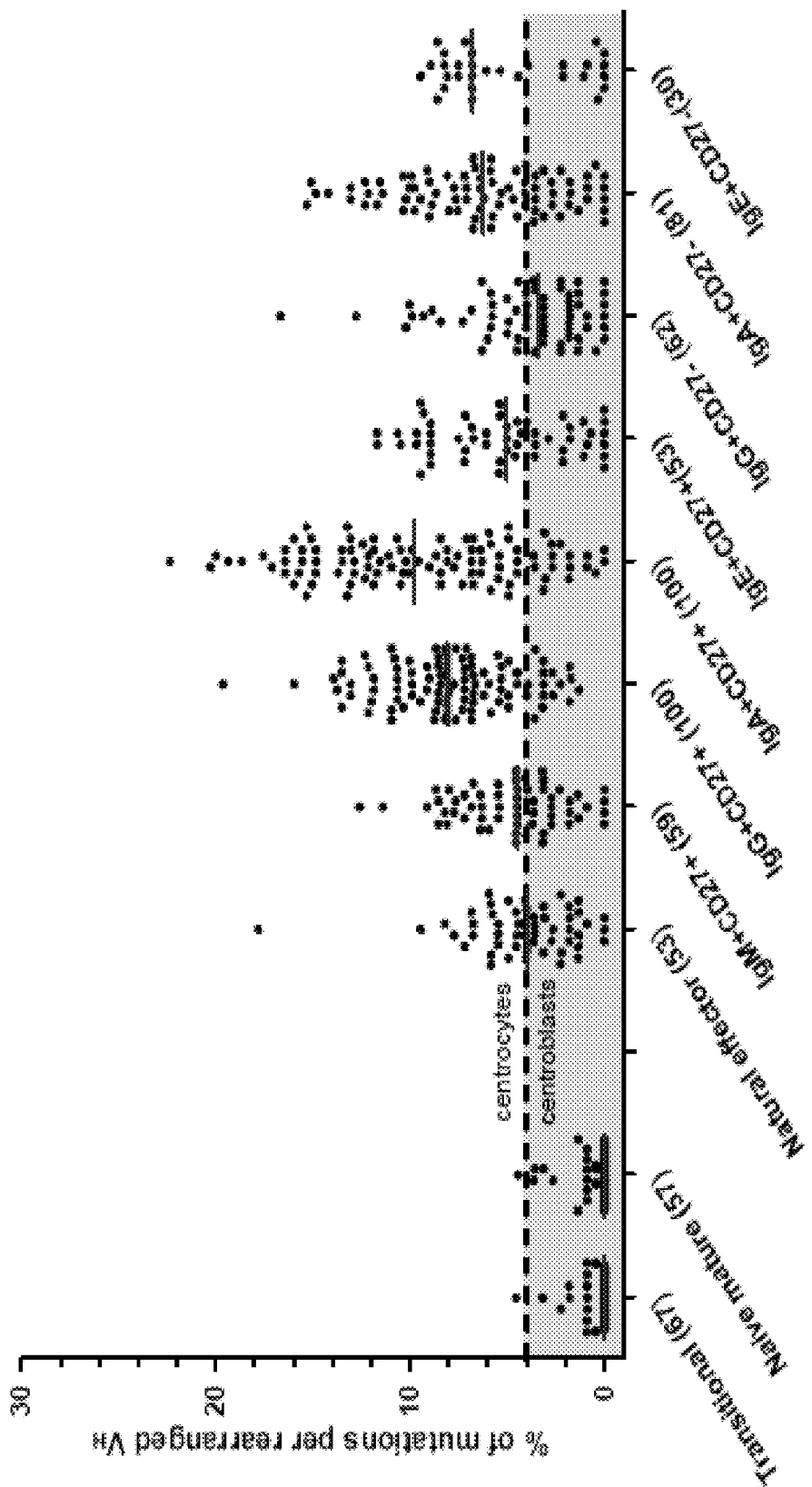
FIG. 3C: mutations per rearranged VH. CD27+IgE+ memory B cell showed similar replication history and SHM characteristics as CD27+IgM+ and CD27±−IgG+ memory B cell subsets that have undergone primary germinal center responses. In contrast, CD27−IgE+ memory B cells had reduced replication history and mutated Vκ3-20 alleles. These characteristics were highly similar to those of CD27-IgA+ memory B cells that have undergone germinal center-independent responses.

Using the above-described strategy, we quantified the CD27−IgE+ and CD27+IgE+ memory B cells in cord blood of 12 neonates, and in blood of 15 children and 23 adults. In general, the numbers of CD27−IgE+ memory B cells were higher than CD27+IgE+ memory B cells. Once the patients were grouped into multiple age categories (1-4 yr, 5-9 yr, 10-19 yr, 20-39 yr, 40-60 yr), we found that the numbers of both CD27−IgE+ and CD27+IgE+ cells increase with peaks at 1-4 yr and 5-9 yr, respectively (FIG. 2). Subsequently, the numbers decrease steadily with about similar numbers in 40-60 yr old adults as compared with neonatal cord blood (FIG. 2). Thus, IgE+ memory B cells can be reliably detected in neonatal, childhood and adult blood, with peak levels in early childhood.

The Origin and Maturation Pathways of IgE+ Memory B Cells

Typical hallmarks of memory B cells are extensive antigen-induced proliferation and SHM. We previously showed that, as a mean, GC B cells in tonsils from young children have undergone ~8 cell cycles, by calculating the ratio between genomic coding joints and signal joints on kappa-deleting recombination excision circles (KREC) of the IGK-deleting rearrangement (van Zelm et al. 2007 J Exp Med 204:645-655). Subsequent analysis of memory B cells in blood of healthy controls showed clear differences between the subsets, which were accompanied by different degrees of SHM in their Ig loci (Berkowska, M. A. et al. 2011. Blood: doi:10.1182/blood-2011-1104-345579). We quantified the replication history, frequency of mutated nucleotides in rearranged IGHV genes and the frequency of mutated IGKV3-20 alleles in CD27+IgE+ and CD27−IgE+ memory B cell subsets. CD27+IgE+ memory B cells had a high replication history of ~10 cell cycles, accompanied by moderately high SHM loads in IGHV genes and high frequencies of mutated IGKV3-20 alleles. These results were most comparable to CD27+IgM+ and CD27−IgG+ memory B cells. The additional similarity of these findings with centrocytes, suggests a germinal center origin for CD27+IgE+ memory B cells.

In contrast, CD27−IgE+ memory B cells showed a low replication history of ~4 cell cycles, accompanied by high SHM loads in IGHV genes and low frequencies of mutated IGKV3-20 alleles. Interestingly, these results were highly similar to CD27−IgA+ memory B cells that originate from germinal center-independent responses in the gut. From this, we hypothesized that CD27+IgE+ memory B cells have a germinal center origin, whereas CD27−IgE+ memory B cells in healthy individuals originate from germinal center-independent responses.

To confirm the germinal center-independent origin of CD27−IgE+ memory B cells, we analyzed their presence in patients with CD40L deficiency. These immunodeficient patients suffer from a hyper-IgM syndrome, due to impaired T-cell dependent B cell responses. Detailed flow cytometric analysis of CD40L deficient patients revealed the presence of IgE+ memory B cells that were mainly CD27-negative (FIG. 4). Thus, we concluded that CD27−IgE+ memory B cells can be generated independently of T-cell help.

We previously found a similar distinction of two IgA+ memory B cells in blood. Similar to the IgE memory B cell subsets, CD27−IgA+ memory B cells displayed molecular signs of a T cell-independent maturation in mucosal tissue and CD27+IgA+ a T cell-dependent maturation. Furthermore, only CD27−IgA+ cells were present in CD40L deficient patients. Several studies have reported signs of active Ig-class switch recombination to IgE in bronchial and nasal mucosa of healthy and allergic subjects. Moreover, allergen-specific IgE can be detected in nasal mucosa. The local production of IgE might be a better correlate with disease than total or allergen-specific serum IgE. Based on our results on IgA± and IgE± memory B cell subsets, we conclude that local mucosal antibody responses can result in the generation of memory B cells. These cells recirculate as CD27−IgA+ or CD27−IgE+ memory B cells. These subsets can therefore reflect local antibody responses in mucosal tissues. Detection of memory B cell subsets, and especially quantification and phenotypic and molecular characterization of the IgE+ memory B cells, can generate insights into allergic diseases, with respect to severity and prediction of future complications.

Increased IgE Memory B Cell Numbers in Blood of Patients with Atopic Dermatitis

Patients suffering from type I hypersensitivity reactions have a skewed IgE repertoire with many secreted IgE molecules recognizing specific allergens. In many patients, the deregulated IgE production can result in increased IgE serum levels. We hypothesize that the skewed IgE repertoire results from altered immune responses, which will be reflected in the memory B cell compartment.

Thus, we analyzed the IgE memory B cell compartment in patients with atopic dermatitis and compared these with healthy controls and patients with psoriasis. Both atopic dermatitis and psoriasis are chronic inflammations of the skin, but in contrast to atopic dermatitis, psoriasis is not IgE-mediated. Therefore, psoriasis patients are not expected to have changes in the IgE memory B cell compartment as compared with controls.

Figure 5:
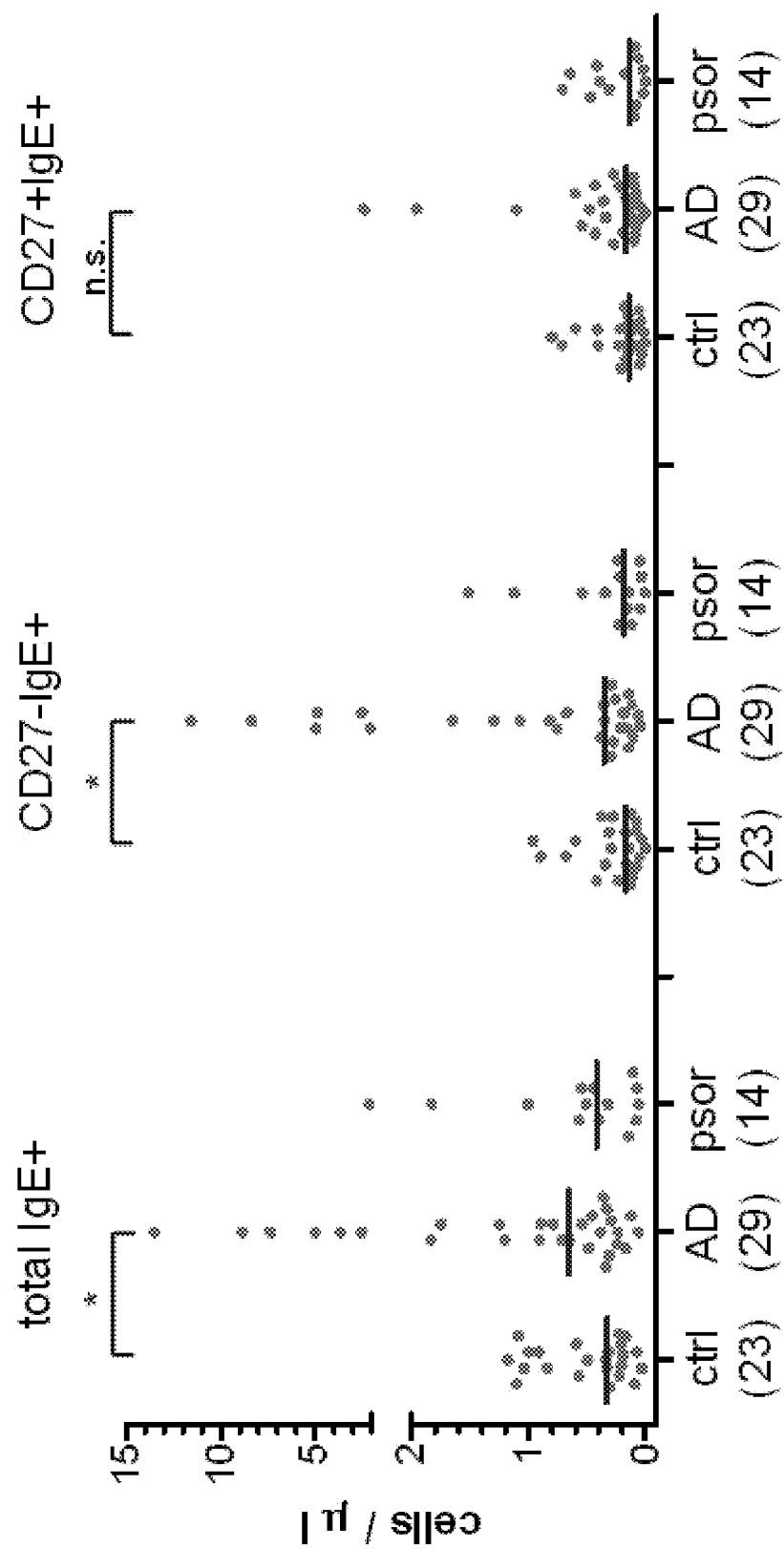
FIG. 5. Frequencies of IgE+ memory B cells in healthy adults (ctrl) and in adult patients with atopic dermatitis (AD) or psoriasis (psor). A large fraction of patients with IgE-mediated atopy showed increased numbers of total IgE+ memory B cells as compared with healthy controls. These mainly reflected an increase of CD27−IgE+ B cells and only few patients showed increased CD27+IgE+ B cells. The frequencies of total IgE+ and CD27−IgE+ B cells were significantly increased in atopy patients as compared with controls. No difference was seen for patients with psoriasis. Bars indicate median values.
Figure 6:
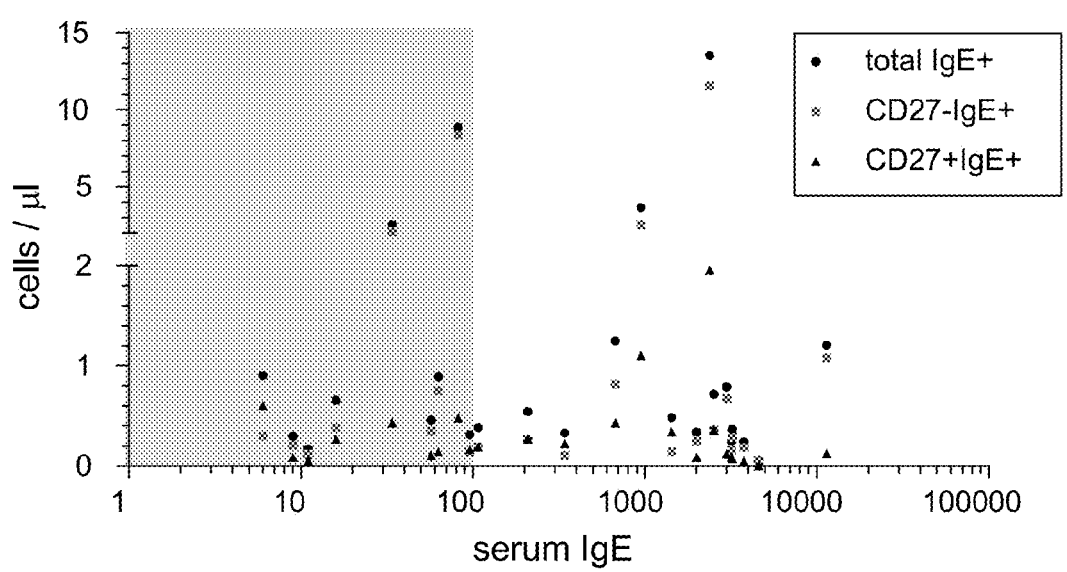
FIG. 6. No correlation between serum IgE levels and IgE memory B cell numbers. The serum IgE levels in 24 AD patients were compared with the IgE+ B cell numbers. Serum IgE levels of >100 U are increased as compared to normal.

Healthy adults (n=23) had 0.0-1.2 IgE+ memory B cells per microliter blood with a median value of 0.33 cells per microliter (FIG. 5). These cells concerned both CD27− and CD27+ subsets in about a 1:1 ratio. Importantly one-third of atopic dermatitis (AD) patients had >1.2 IgE+ memory B cells per microliter blood. These cells mainly concerned an increase in the CD27− subsets, but in some cases the CD27+ subset was increased. The distributions of total IgE+ and CD27−IgE+ memory B cells in AD patients were significantly different as compared to controls. Some patients with psoriasis showed increased IgE+ memory B cells. However, these distributions were not significantly different as compared to controls or AD patients. Increased memory IgE+ B cell numbers in patients with AD were not associated with increased serum IgE levels (FIG. 6). This fits very well with the hypothesis that the CD27−IgE+ memory B cells have been generated in local mucosal tissue. These antibody responses hardly contribute to serum IgE levels. Therefore, memory IgE+ B cell numbers represent a novel disease marker for type 1 hypersensitivity.

Our results show that IgE+ memory B cells and plasma cells can be reliably detected with a multi-color flow cytometric approach that includes antibodies against all 5 Ig isotypes, a B cell marker (e.g. CD19), and CD38 and CD27 to delineate plasma cells and memory B cell subsets. Furthermore, our combined flow cytometric and molecular results show that IgE+ memory B cells can be classified into CD27+IgE+ and CD27−IgE+ subsets that in healthy individuals have undergone either a germinal center-dependent or independent response, respectively. Finally, we show that both CD27+IgE+ and CD27−IgE+ memory B cells are increased in blood of a large group of patients suffering from type 1 hypersensitivity.

We show that our multi-color flow cytometric approach to detect and characterize CD27+IgE+ and CD27−IgE+ memory B cells can be used for classification of type 1 hypersensitivity patients, but also for other immune mediated diseases with suspected involvement of IgE antibodies (e.g. RA) and parasitic infections (Table 2). Furthermore, we claim that our multi-color flow cytometric approach is an excellent method for early monitoring of treatment efficacy, especially with anti-IgE antibodies (Table 2). Since anti-IgE antibodies can recognize IgE that is expressed on memory B cells and plasma cells, they can function to eliminate these IgE+ cells. Although it is thought that anti-IgE treatment with Xolair functions in part through decrease the production of IgE, current experimental techniques to test this are lacking. Finally, our flow cytometric approach can be used to detect allergen-specific IgE+ memory B cells, following incubation with fluorescently-labeled recombinant allergens. Similarly we hypothesize that detection of increased levels of IgE+ memory B cells and/or plasma cells in blood or other body fluids (e.g. cerebrospinal fluid) may also reflect an undergoing type I hypersensitivity response.

TABLE 2

Exemplary applications for quantification and characterization of IgE+ memory B cells and plasma cells.

| Condition | Examples |
| --- | --- |
| Type 1 (IgE-mediated) allergies | Asthma Hay fever (rhinitis) Food allergies Atopic dermatitis Drug-associated allergy (e.g. anaphylaxis) |
| Autoimmune diseases | Rheumatoid Arthritis Graves' Disease Systemic Lupus Erythematosus |
| Primary Immunodeficiencies with Hyper-IgE serum levels | Genetic deficiencies of: DOCK8, TYK2, STAT3 |
| Parasitic infections | Helminths |
| Therapy monitoring | Anti-IgE (omalizumab/Xolair) treatment Anti-IgE (47H4; anti-M1') treatment Allergen-specific immunotherapy (oral or subcutaneous applications) |

The invention claimed is:

1. A multi-color flow cytometric method for analyzing memory B cell and plasma cell subsets in a biological sample from a subject, comprising the steps of:
   (i) staining the sample with an antibody cocktail comprising fluorochrome-conjugated antibodies, said antibody cocktail comprising antibodies against IgM, IgA, IgG, IgD and IgE, an antibody against a B cell marker and an antibody against the CD38 antigen, wherein each of said antibodies in said antibody cocktail is conjugated to a different fluorochrome than the other antibodies, or wherein antibodies selected from the group consisting of anti-IgA, anti-IgE and anti-IgG are conjugated with a total of two fluorochromes, wherein a first antibody selected from the group consisting of anti-IgA, anti-IgE and anti-IgG is conjugated to a first fluorochrome, a second antibody selected from the group consisting of anti-IgA, anti-IgE and anti-IgG is conjugated to a second, distinct fluorochrome and the third antibody selected from the group consisting of anti-IgA, anti-IgE and anti-IgG is conjugated simultaneously to the first and second fluorochrome;
   (ii) subjecting the sample to multicolor flow cytometry and gating for lymphocytes based on forward scatter and side scatter pattern;
   (iii) gating the lymphocytes for expression of the B cell specific marker to identify B cells, and for expression of CD38 to identify a memory B cell population having diminished CD38($CD38^{dim}$) expression and a plasma cell population having high CD38 ($CD38^{hi}$);
   (iv) determining surface expression of IgM, IgA, IgG, IgD and IgE on the cells in said identified memory B cell population and/or said plasma cell population; and
   (v) detecting and quantitating the IgE+ cells within the memory B cell population and/or the plasma cell population by the negative selection of cells expressing IgM, cells expressing IgA, cells expressing IgG and cells expressing IgD, and the positive selection of IgE expressing cells.

2. The method according to claim 1, wherein the B cell marker is CD19, CD20, CD79a or CD22 antigen.

3. The method according to claim 1, wherein the panel of fluorochrome-conjugated antibodies comprises, in addition to said B cell marker, at least one further fluorochrome-conjugated antibody reactive with a B cell antigen.

4. The method according to claim 3, wherein the further B cell antigen is a marker for characterization of memory B cells.

5. The method according to claim 3, wherein the further B cell antigen is a marker for characterization of plasma B cells.

6. The method according to claim 3, wherein the B cell antigen is a marker selected from the group consisting of CD23, CD40, CD80, CD86, CD180, transmembrane activator and CAML interactor (TACI), CD200, CD73, T-cell leukemia/lymphoma protein-1 (TCL1) and CD62L.

7. The method according to claim 3, wherein the further B cell antigen is a marker for characterization of plasma B cells and is CD20 or CD138 antigen.

8. The method according to claim 1, wherein the biological sample is blood, bone marrow, lymphoid tissue, tears, cerebrospinal fluid, saliva or fluid from skin vesicles.

9. The method according to claim 1, further comprising at least one step of characterizing the IgE+ memory B cell population and/or the IgE+ plasma cell population.

10. The method according to claim 9, wherein characterizing comprises staining the cells with an anti-CD27 antibody and detecting within the IgE+ memory B cell population the CD27+ and CD27- memory B cell subsets.

11. The method according to claim 9, wherein characterizing comprises determining the antigen specificity of the IgE+ memory B cell population and/or the IgE+ plasma cell population by contacting the cells with a fluorochrome-conjugated antigen of interest.

12. The method according to claim 9, wherein the antigen of interest is an allergen.

13. The method according to claim 1, wherein the B cell marker is CD19 antigen.

14. The method according to claim 1, wherein said two fluorochromes are fluorescein isothiocyante (FITC) and phycoerythrin (PE).

15. A method to diagnose and/or classify a disease or condition associated with altered IgE levels and IgE specificity, comprising analyzing memory B cell and plasma cell subsets in a biological sample isolated from a subject according to the method of claim 1, further comprising the step of correlating the amount of IgE+ plasma and/or IgE+ memory B cells with the disease diagnosis and/or classification, wherein an increased number of IgE+ memory B cells and/or plasma cells as compared to healthy controls without disease or conditions associated with altered IgE levels and IgE specificity is indicative of the subject suffering from the disease.

16. The method according to claim 15, wherein the disease is selected from the group consisting of type 1 hypersensitivity, an immune disease with suspected involvement of IgE antibodies.

17. The method according to claim 15, wherein said type 1 hypersensitivity is selected from the group consisting of asthma, hay fever (rhinitis), food allergy, and atopic dermatitis, wherein said immune disease with suspected involvement of IgE antibodies is selected from the group consisting of rheumatoid arthritis (RA), mastocytosis, Graves disease and systemic lupus erythematosis (SLE), and wherein said parasitic infection is a helminth infection.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: IGHA reverse primer

<400> SEQUENCE: 1
gtggcatgtc acggacttg                                           19

<210> SEQ ID NO 2
<211> LENGTH: 19
<212> TYPE: DNA
<213> ORGANISM: Artificial Sequence
<220> FEATURE:
<223> OTHER INFORMATION: IGHG reverse primer

<400> SEQUENCE: 2
cacgctgctg agggagtag                                           19

<210> SEQ ID NO 3
<211> LENGTH: 24
<212> TYPE: DNA
<213> ORGANISM: Artificial Sequence
<220> FEATURE:
<223> OTHER INFORMATION: IGHE reverse primer

```
<400> SEQUENCE: 3
catcaccggc tccgggaagt agcc                                              24

<210> SEQ ID NO 4
<211> LENGTH: 22
<212> TYPE: DNA
<213> ORGANISM: Artificial Sequence
<220> FEATURE:
<223> OTHER INFORMATION: IGHE reverse primer

<400> SEQUENCE: 4
gtttttgcag cagcgggtca ag                                                22
```